United States Patent [19]
Mikulec et al.

[11] Patent Number: 5,878,153
[45] Date of Patent: Mar. 2, 1999

[54] METHOD FOR MONITORING COATING ADHESION PROPENSITY BASED ON SURFACE MORPHOLOGY

[75] Inventors: Michelle Jarmilla Mikulec, Dearborn; John Xiaoyang Li, Sterling Heights; Mark Paul Everson, Canton, all of Mich.

[73] Assignee: Ford Global Technologies, Inc., Dearborn, Mich.

[21] Appl. No.: 709,947

[22] Filed: Sep. 9, 1996

Related U.S. Application Data

[63] Continuation-in-part of Ser. No. 265,856, Jun. 24, 1994, abandoned.

[51] Int. Cl.⁶ .................................................. G06K 9/00
[52] U.S. Cl. ........................................ 382/108; 382/152
[58] Field of Search .................................. 382/108, 141, 382/152; 348/86, 90; 356/376, 378, 380, 381, 237

[56] References Cited

U.S. PATENT DOCUMENTS

| | | | |
|---|---|---|---|
| 3,984,189 | 10/1976 | Seki et al. ................................... | 356/73 |
| 4,099,884 | 7/1978 | Nash ........................................ | 356/200 |
| 4,395,683 | 7/1983 | Liptay-Wagner et al. .............. | 358/166 |
| 4,629,319 | 12/1986 | Clarke et al. ............................ | 356/237 |
| 4,841,364 | 6/1989 | Kosaka et al. ........................... | 358/101 |
| 4,853,777 | 8/1989 | Hupp ....................................... | 358/107 |
| 4,863,268 | 9/1989 | Clarke et al. ............................ | 356/237 |
| 4,896,278 | 1/1990 | Grove ...................................... | 364/552 |
| 4,920,385 | 4/1990 | Clarke et al. ............................ | 356/237 |
| 5,041,726 | 8/1991 | Chang et al. ............................ | 250/341 |
| 5,073,951 | 12/1991 | Hayashi .................................. | 382/141 |
| 5,086,232 | 2/1992 | Maguire et al. ......................... | 250/572 |
| 5,094,600 | 3/1992 | Sikora ..................................... | 425/113 |
| 5,125,746 | 6/1992 | Lipshitz .................................. | 356/376 |
| 5,153,445 | 10/1992 | Stapleton ................................ | 250/572 |
| 5,168,322 | 12/1992 | Clarke et al. ............................ | 356/237 |
| 5,229,835 | 7/1993 | Reinsch .................................. | 356/371 |
| 5,249,029 | 9/1993 | Sommer et al. ........................ | 356/336 |
| 5,274,713 | 12/1993 | Chang et al. ............................ | 382/8 |
| 5,275,768 | 1/1994 | Inaba et al. ............................. | 264/40.1 |
| 5,283,018 | 2/1994 | Inaba et al. ............................. | 264/40.1 |
| 5,327,286 | 7/1994 | Sampsell et al. ....................... | 359/561 |
| 5,377,001 | 12/1994 | Malin et al. ............................ | 356/237 |
| 5,379,347 | 1/1995 | Kato et al. ............................... | 382/8 |
| 5,416,589 | 5/1995 | Lysogorski ............................. | 356/371 |
| 5,438,525 | 8/1995 | Shimbara ................................ | 382/141 |
| 5,440,648 | 8/1995 | Roberts et al. .......................... | 382/8 |
| 5,477,268 | 12/1995 | Shimbara et al. ...................... | 348/128 |
| 5,566,244 | 10/1996 | Kato et al. ............................... | 382/108 |

OTHER PUBLICATIONS

Hopfield, John, J., "Neurons, Dynamics and Computation", Physics Today, Feb., 1994, pp. 40–46.

*Primary Examiner*—Christopher S Kelley
*Attorney, Agent, or Firm*—Damian Porcari; Roger L. May

[57] ABSTRACT

A method for monitoring process parameters in a multiple step process for an article molded from a plastic material containing at least two constituents to determine propensity for adhesion of a subsequently applied coating includes imaging at least one region of the article to examine surface morphology and analyzing the surface morphology to identify one of the constituents. In a preferred embodiment, the method is applied to monitor a manufacturing process for a molded plastic bumper to determine adhesion propensity of a subsequently applied adhesion promoter or paint based on surface morphology of the component. Analysis of the surface morphology includes identifying the presence of rubber globules near the surface layer or skin.

8 Claims, 2 Drawing Sheets

METHOD FOR MONITORING COATING ADHESION PROPENSITY BASED ON SURFACE MORPHOLOGY

CROSS-REFERENCE TO RELATED APPLICATION

This application is a continuation-in-part application of currently application Ser. No. 08/265,856 now abandoned, filed Jun. 24, 1994, the disclosure of which is hereby incorporated by reference in its entirety.

TECHNICAL FIELD

The present invention relates to a method for monitoring process parameters based on surface morphology of parts, especially plastic parts, during manufacturing so as to determine adhesion propensity of subsequently applied coatings, such as paint.

BACKGROUND ART

Manufacture of automotive components is continually plagued by seemingly conflicting requirements for engineering materials. For example, various components may be required to possess certain structural characteristics while also being lightweight, durable, aesthetic, and easily manufactured and assembled. Compromises are often made to optimize the most important properties of each component. Alternatively, new materials and processes are continually developed to enhance desirable properties while reducing or eliminating less desirable characteristics.

Plastics have emerged as generally possessing desirable attributes for a variety of automotive applications. Unfortunately, properties which make certain plastics desirable for use in automotive components, such as body panels, fascia, wheel covers, and the like, also result in poor adhesion characteristics for subsequently applied coatings, such as paint or metallic films. The material properties may be altered by introducing additives to enhance adhesion characteristics, varying the coating process, or both.

Once an acceptable material formulation and coating process are developed, it is desirable to implement an appropriate quality assurance procedure to consistently maintain the desirable component characteristics. The quality assurance procedure should identify any nonconforming components as early as possible in the manufacturing process to minimize the expense of time and materials which may be incurred during subsequent manufacturing, or due to customer dissatisfaction manifested in warranty repairs. Preferably, the quality assurance procedure is capable of identifying a particular step or process parameter responsible for a nonconforming component so that prompt corrective action may be instituted whether by the compounder, the part manufacturer (i.e. the molder) or the processor (applying the coating).

Material properties of plastic components may be monitored using any of a number of destructive or nondestructive testing techniques. Destructive testing techniques, such as scanning electron microscopy, are not amenable to use in high-volume manufacturing applications because they are generally time consuming and destroy the part during testing. However, such techniques are useful for gathering various sample data which may be used to investigate material properties or verify on-line testing techniques.

Nondestructive testing of coated or painted surfaces is often performed via visual inspection, either manually or automatically by computer vision/image processing systems. These systems detect defects or flaws which may be present in the coating or on the surface of the substrate. However, changes in plastic material formulation or processing may not be manifested in defects readily apparent from traditional examination of the coating. Undetected changes may then result in subsequent chipping or peeling of the coating from the substrate due to improper adhesion when the component is subjected to impact, abrasion, heat, or the like.

SUMMARY OF THE INVENTION

It is an object of the present invention to monitor process parameters for an article molded from a plastic material to determine or predict propensity for adhesion of a subsequently applied coating based on changes in the surface morphology of the article.

It is another object of the present invention to provide a method for manufacturing a plastic automotive component which includes analyzing the surface morphology of the component to monitor and control curing temperature and time of the component to improve adhesion propensity of a subsequently applied coating.

It is a further object of the present invention to provide a method for monitoring the manufacturing of a plastic part containing rubber which analyzes surface morphology of the part to determine the presence of rubber as an indication of adhesion propensity of a subsequently applied coating.

Yet another object of the present invention is to provide a method for inspecting plastic articles which correlates changes in surface morphology to coating adhesion performance in thermal shock tests or other similar performance evaluations.

Another object of the present invention is to monitor surface morphology to determine appropriate pretreatment parameters and processes.

In carrying out these and other objects of the present invention, a method is provided for inspecting a molded plastic article formed of at least two constituent materials to determine propensity for adhesion of a subsequently applied coating. The method includes imaging at least one region of the article to examine surface morphology of the at least one region, analyzing the surface morphology of the at least one region to identify at least one of the at least two constituent materials, and determining the propensity for adhesion of the subsequently applied coating to the article based on the surface morphology.

A method is also provided for manufacturing an automotive component molded from a thermoplastic polyolefin material containing rubber to determine propensity for adhesion of a paint coating subsequently applied to the component. The method includes molding the component with at least one inspection surface region positioned on a non-show area of a completed component, applying an adhesion promoter to the component to improve adhesion propensity of the paint coating, and heating or curing the component for a predetermined period of time. The method also includes imaging the at least one inspection surface region with a sufficient magnification to create a morphological image of the at least one surface region, analyzing the morphological image to identify presence of rubber to determine the propensity for adhesion of the paint coating to be subsequently applied, and modifying the step of heating the component to increase the propensity for adhesion based on the step of analyzing.

In a preferred embodiment, the method of the present invention is utilized to monitor manufacturing processes of a molded plastic bumper to determine adhesion propensity of paint so as to reduce warranty repairs due to paint peeling or chipping.

The advantages accruing to the present invention are numerous. For example, the present invention provides a nondestructive testing technique which is amenable to inspection of high volume automotive components. The present invention identifies changes in surface morphology of plastic molded parts to identify potential coating adhesion failures which would not be otherwise apparent from a visual inspection, such as changes in the molecular weight and distribution of polymers present at the surface, chain length, and the like. By identifying potential coating adhesion failures, the present invention reduces scrap in molding and coating processes and lowers customer complaints by improving coating quality. The present invention also allows inspection of raw or bulk materials to assure proper characteristics prior to expending additional labor and materials for subsequent manufacturing.

The above objects and other objects, features, and advantages of the present invention will be readily appreciated by one of ordinary skill in the art from the following detailed description of the best mode for carrying out the invention when taken in connection with the accompanying drawings.

BEST MODE(S) FOR CARRYING OUT THE INVENTION

The present invention determines the propensity for adhesion of coatings applied to plastic components, particularly automotive components, based on an analysis of the surface morphology of the components. As used in this description, surface morphology refers to the form and structure of the material and/or its constituents which exist at or near the surface.

Many plastic articles utilized in automotive applications require multiple step processes to produce a finished article. Some processes may alter the surface morphology of the article while others may not. Similarly, depending upon the particular process, one particular change in surface morphology may be desirable while another is undesirable or of no consequence. The present invention may be used to monitor process parameters for any process which affects the surface morphology of the article when the process is out of control by monitoring changes in the surface morphology from piece to piece or relative to an established reference. Prior to component processing, the present invention may be used to determine quality of the raw material based on a predetermined desirable surface morphology.

In a preferred embodiment, the present invention is utilized with plastic materials used to form various automotive components, particularly bumpers and fascia. Any other part to which a coating, such as paint or metallic film, is subsequently applied may also be suitable for application of the present invention. Plastics which are currently used include polyolefins such as polyethylene, polypropylene, polybutadiene, and copolymers thereof, such as ethylene propylene, and the like. A particular preferred class of materials is referred to as thermoplastic polyolefins (TPO). Other materials include polycarbonates, polyurethanes, polyesters, acrylics, polyvinyl, such as PVC or polyvinyldiene chloride, polyamides (such as nylon), and engineering plastics such as polyphenylene sulfide, polysulfone, polybenzimidazole, and the like.

Figure 1:
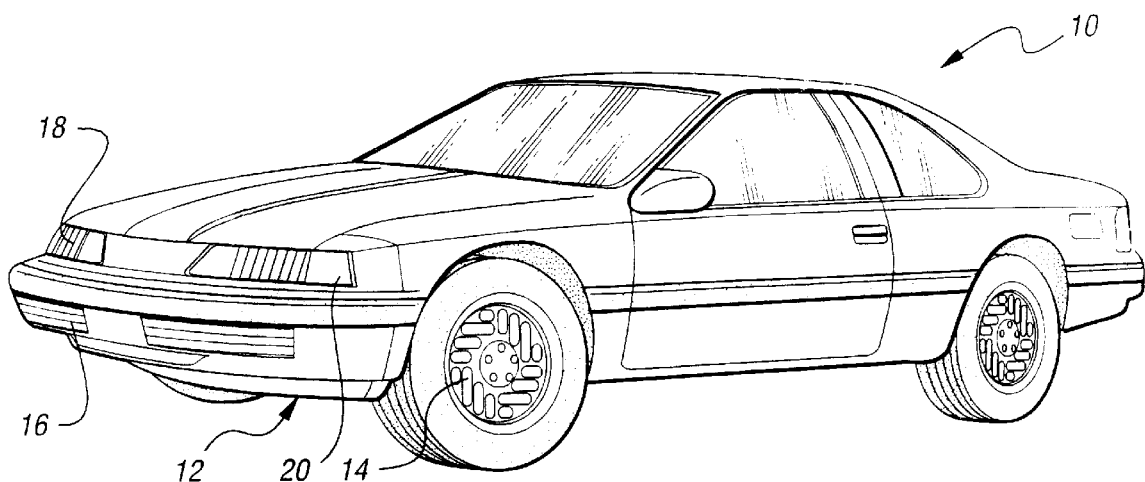
FIG. 1 is a pictorial representation of an automobile illustrating various molded plastic components manufactured according to the present invention.

Referring now to FIG. 1, an automobile 10 illustrates various components which may be manufactured according to the present invention. Automobile 10 includes various body panels, such as front fascia 12, which may be made from molded plastic and subsequently coated with paint as described below. Similarly, wheel cover 14 may include a molded plastic substrate which is subsequently coated with a metallic film, paint, or both. Front fascia 12 may function as an integrated bumper as shown. When molded, front fascia 12 may include various regions or areas which are subsequently modified during manufacturing and assembly to accommodate air intakes (or a grill) 16, headlamps 18, turn indicators 20, and the like present in the final product.

Figure 2:
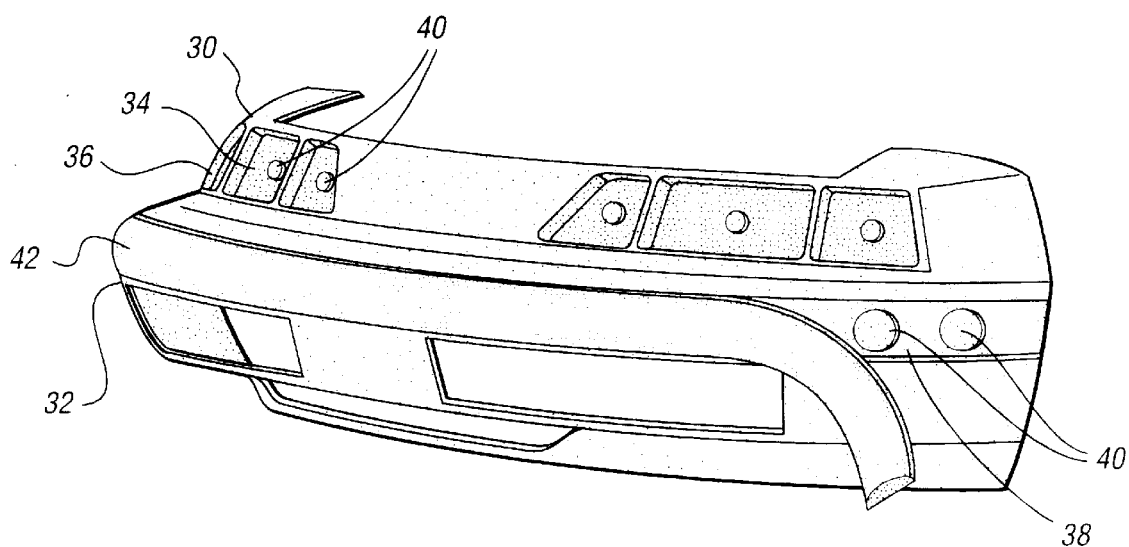
FIG. 2 is a molded plastic fascia illustrating positioning of inspection regions in non-show areas.

Referring now to FIG. 2, an alternative front fascia 30 is shown prior to assembly. Front fascia 30 includes various "show" areas, such as bumper 32 and other "non-show" areas, such as headlamp cutout 34, turn indicator cutout 36, and groove 38. Rub strip 42 is located in groove 38 and fixed to fascia 30 during assembly. Show areas are those which are in plain or ordinary view to a casual observer on the completed product or article. Non-show areas or regions are those which are either removed during manufacturing, such as headlamp cutout 34, covered by another component, such as groove 38, or are hidden from ordinary view, such as the back side of bumper 32.

FIG. 2 also illustrates positioning of one or more test regions 40 according to the present invention. Each test region 40 is preferably positioned on a non-show area of the article and is formed during molding specifically for inspection of surface morphology of the article according to the present invention. In a preferred embodiment, each test region 40 is about 6.5 cm$^2$ (1 in$^2$) and is slightly raised above the surrounding surface to facilitate locating for automated inspection. Preferably, a number of test regions 40 are positioned about fascia 30 in various non-show areas to detect localized variations in material surface morphology.

Test regions 40 preferably have a molded surface finish corresponding to an SPI #3 or SPI #4 finish as determined by the Society of Plastics Institute, or equivalent. This allows on-line inspection of the surface morphology of the molded article without additional sample preparation. Alternatively, samples may be removed from front fascia 30 and appropriately prepared for inspection of surface morphology according to the present invention.

Figure 3:
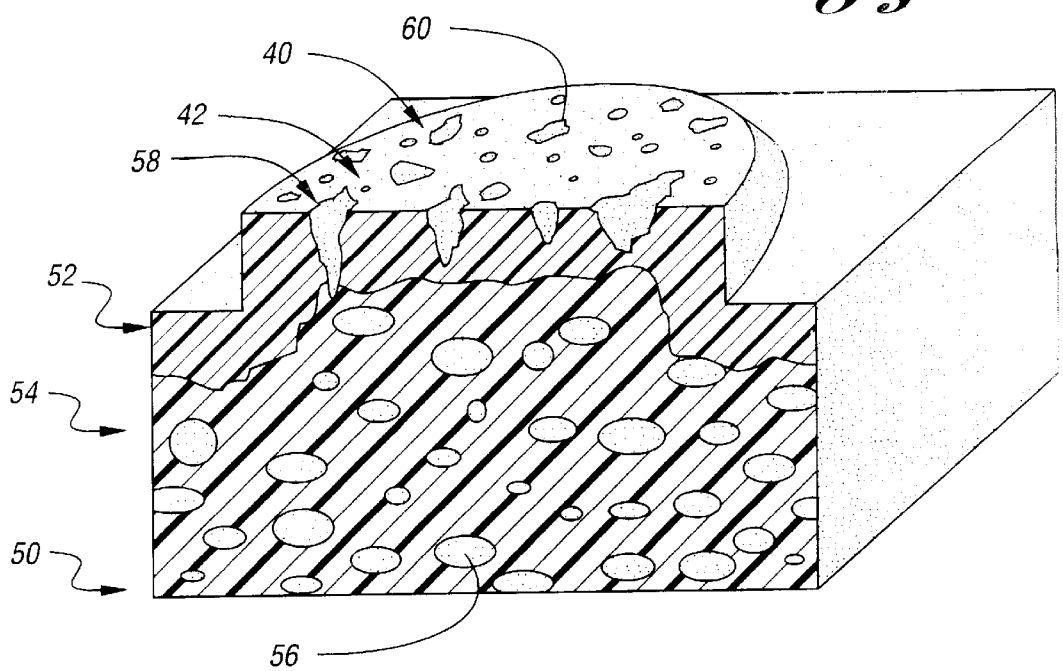
FIG. 3 is a pictorial representation in partial cross-section of an inspection region of a molded plastic part illustrating surface morphology features in addition to bulk material features.

A schematic representation of material structure illustrating examination of surface morphology according to the present invention is shown in FIG. 3. Sample 50 represents a magnified sample area shown in partial cross-section to illustrate the material structure and organization of a representative molded plastic article. Sample 50 includes a skin layer 52 (uppermost stratum) which is an integral part of the TPO bulk formed during cooling of the melt. In a preferred embodiment, skin layer 52 extends between 1 and 5 microns below the surface. For a TPO material, skin layer 52 includes mostly low molecular weight species which is different from the bulk layer 54 which includes ethylene propylene rubber globules 56 in an amorphous polypropylene matrix. Formation of skin layer 52 depends on the rate of tool (mold) cooling.

The present invention preferably utilizes a visual inspection of surface 42 of test region 40, such as done in reflective microscopy. A sufficient magnification is used to create a morphological image showing surface features 60 in contrast to surrounding, background area 42. Surface features 60 may be represented by dark areas with background area 42 represented by light areas, or vice versa. In a preferred embodiment, a magnification between 100× and 200× is used with 200× being most preferable. However, magnification level may vary depending upon the particular material, coating process, and imaging equipment.

The present invention began by developing a baseline surface morphology for uncoated molded plastic articles. Over 5000 morphological images were examined to determine the effects of variations in material, pretreatments, and coating processes (particularly curing temperatures) on surface morphology of various articles. A typical manufacturing process may include pretreatment followed by one or more subsequent coating applications. Pretreatment may include power washing, drying, applying an adhesion promoter, flame and plasma treatments, and curing at a predetermined temperature (e.g. between 170° F. and 250° F.) for a predetermined time (e.g. 10–30 minutes). Alternatively, a lower curing temperature may be used followed by flash off of solvents in the adhesion promoter. One or more coatings are then applied and may be cured at an appropriate temperature for a predetermined time. It was determined that some pretreatment processes, such as power washing, do not affect the surface morphology while others, such as curing affect the surface morphology as described below.

Changes observed in surface morphology were then correlated to coating adhesion performance as indicated by thermal shock tests and other similar tests. Destructive testing techniques, such as differential scanning calorimetry and atomic force microscopy verified the changes in material structure within and adjacent to the surface layer as manifested in the surface morphology. Thus, the present invention uses surface morphology of a plastic article formed of at least two constituent materials to determine propensity for adhesion of the subsequently applied coating(s).

One particular mechanism for adhesion of a subsequently applied coating may be explained also with reference to FIG. 3. In a preferred embodiment, a TPO material commercially available from D&S of Auburn Hills, Mich., identified as D-161 was analyzed to determine the effect of one type of pretreatment. The D-161 material includes polypropylene, polyethylene, ethylene propylene, rubber, carbon black, talc, a UV stabilizer and a thermostabilizer. The sample was injection molded to a plaque 6 inches by 4 inches and subjected to a severe trichloroethane (TCE) treatment for 5 minutes (twice) and baked at 190° F. The polymers of the surface layer were dissolved by the TCE solvent and recrystallized during solvent evaporation. During solvent application, rubber globules 56 swell and rise to the surface through skin layer 52. As the solvent evaporates, globules 56 shrink and retract leaving craters 58 in the surface. This exposes the rubber globules located in the layer below skin 52 to change the characteristics of TPO from non-polar to polar thus improving adhesion propensity for subsequently applied coatings. The rubber globules (or craters formed by them) typically appear as dark round features in the morphological image as represented by surface features 60.

Adhesion propensity of the uppermost stratum may also be modified by mechanical abrasion with solvent (isopropyl alcohol—IPA) wiping. This exposes the rubber globules such that the uppermost stratum of the TPO becomes polar so as to enhance adhesion of subsequently applied paint. This change to the surface morphology is visible at 100× magnification.

In a preferred embodiment, an adhesion promoter is applied to the molded product prior to coating. The adhesion promoter contains a resin carried by an aromatic solvent having high content of toluene and xylene. The solvents cause swelling of the rubber globules as described above. As the solvent evaporates during curing (or is flashed off), the rubber retracts and mechanically entangles the adhesion promoter in craters 58 to adhere to the surface. Subsequently applied coatings, such as paint or a clear coat then adhere to the adhesion promoter resin.

Figure 4:
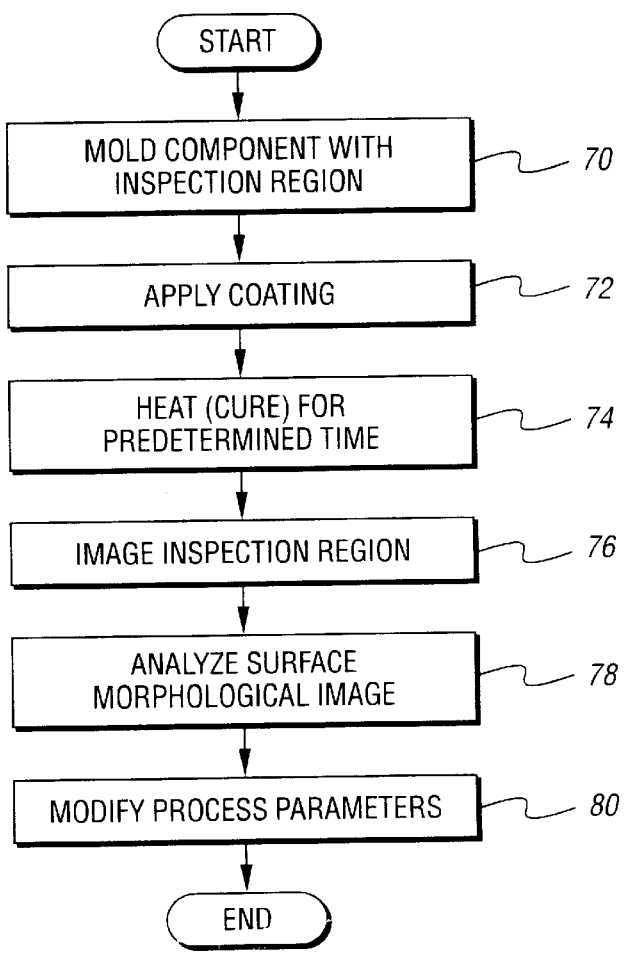
FIG. 4 is a flowchart illustrating a method for manufacturing a molded plastic article using surface morphology analysis according to the present invention.

The flowchart of FIG. 4 summarizes the steps of a method according to the present invention as described above with reference to FIGS. 1–3. Block 70 represents molding a plastic article or component with one or more inspection regions preferably located to be hidden from plain view on a completed article, i.e. in a non-show area. The inspection areas may be molded with a polished (smooth) surface to facilitate on-line inspection, or may be removed for subsequent sample preparation. A coating is applied as represented by block 72 and heated at a cure temperature for a predetermined period of time as represented by block 74.

One or more of the inspection regions is imaged with a sufficient magnification to create a morphological image as represented by block 76. This image is then analyzed to determine the propensity for adhesion of the coating. Based on this analysis, the process parameters which should be adjusted are determined as represented by block 80. Process parameters may include the heating temperature or time, material composition, solvent content, or the like. Modification of process parameters may be completed automatically by a process control computer or an operator may be alerted that the process is not within predetermined control parameters.

Of course, blocks 76, 78, and 80 may be performed after any process which affects the surface morphology of the article. As such, these steps may be performed prior to applying a coating to the surface to determine adhesion propensity of the subsequently applied coating. As such, modification of process parameters as represented by step 80 would then apply to subsequently processed articles.

During development of the present invention, it was determined that a human observer analyzing morphological images could determine variations due to a change in only a single process parameter (such as temperature). However, actual processing includes several variable parameters in material composition, injection molding, pretreatment, and coating processes which make analysis of surface morphology to determine adhesion propensity difficult for a human observer. As such, in a preferred embodiment automated imaging and analysis of morphological images is performed by computer pattern recognition. Various well established image processing techniques may be used to identify acceptable surface morphologies, such as statistical pattern recognition, matched filtering, knowledge or rule based processing, classifiers, or neural networks. A preferred embodiment of the present invention utilizes a neural network to classify surface morphology of various images. A database of images may be collected to train the neural network using examples of acceptable and unacceptable surface morphologies based on thermal shock performance, or other suitable indicator. Training sets may vary depending upon the particular plastic component and coating processes employed. Other parameters which may affect the surface morphology include tool surface temperature, heat transmission throughout and within the part, spacing of the part relative to a heating surface, and material flow.

While the method illustrated in FIG. 4 represents a typical application of the present invention for a manufacturer which processes a molded plastic article, the present invention may also be used to monitor the compounding process of purchased parts suppliers. A typical process may include mixing ingredients, pelletizing, molding plaques for inspection, imaging surface morphology, and modifying plastic formulation based on the surface morphology. Of course, other processes which have a positive correlation between surface morphology and process control are also appropriate for application of the present invention.

While the forms of the invention herein disclosed constitute presently preferred embodiments, many others are possible. It is not intended herein to mention all of the possible equivalent forms or ramifications of the invention. It is understood that the terms used herein are merely descriptive rather than limiting and that various changes may be made without departing from the spirit or scope of the invention.

What is claimed is:

1. A method for monitoring process parameters in a multiple step process for an article molded from a plastic material including a t least polypropylene and rubber to determine propensity for adhesion of a coating subsequently applied to the article wherein the process includes at least one step which affects surface morphology of the article, the method comprising:

molding the article with at least one highly polished surface region located to be hidden from plain view on a completed article;

imaging the at least one highly polished surface region with a sufficient magnification to create a morphological image of the at least one highly polished surface region;

analyzing the morphological image to determine the propensity for adhesion of the coating to be subsequently applied; and determining the process parameters which should be adjusted, including at least one of plastic composition, heating temperature, and heating time, to increase the propensity for adhesion based on content of the morphological image.

2. The method of claim 1 further comprising removing the at least one highly polished surface region from the article prior to the step of imaging.

3. The method of claim 1 further comprising covering the at least one highly polished surface region with an opaque object after the step of imaging.

4. The method of claim 1 wherein the step of analyzing comprises determining a ratio of dark surface area to light surface area in the morphological image.

5. The method of claim 1 wherein the subsequently applied coating includes paint and wherein the step of analyzing comprises determining quantity of rubber represented in the morphological image.

6. A method for manufacturing an automotive component molded from a thermoplastic polyolefin material containing rubber to determine propensity for adhesion of a paint coating subsequently applied to the component, the method comprising:

molding the component with at least one inspection surface region positioned on a non-show area of a completed component;

applying an adhesion promoter to the component to improve adhesion propensity of the paint coating;

heating the component for a predetermined period of time;

imaging the at least one inspection surface region with a sufficient magnification to create a morphological image of the at least one surface region;

analyzing the morphological image to identify presence of rubber to determine the propensity for adhesion of the paint coating to be subsequently applied; and modifying the step of heating the component to increase the propensity for adhesion based on the step of analyzing.

7. The method of claim 6 wherein the step of modifying comprises modifying temperature of the component during the step of heating.

8. The method of claim 6 wherein the step of modifying comprises modifying the predetermined time period.

* * * * *